United States Patent [19]

Hansen, Jr. et al.

[11] Patent Number: 5,389,645

[45] Date of Patent: Feb. 14, 1995

[54] SUBSTITUTED TYROSYL DIAMINE AMIDE COMPOUNDS

[75] Inventors: Donald W. Hansen, Jr., Skokie; Nizal S. Chandrakumar; Karen B. Peterson, both of Vernon Hills; Sofya Tsymbalov, Des Plaines, all of Ill.

[73] Assignee: G. D. Searle & Co., Chicago, Ill.

[21] Appl. No.: 929,275

[22] Filed: Aug. 13, 1992

[51] Int. Cl.$^6$ .................... C07D 215/48; A61K 31/47
[52] U.S. Cl. ..................................... 514/311; 546/169
[58] Field of Search ......................... 546/169; 514/311

[56] References Cited

U.S. PATENT DOCUMENTS

| | | | |
|---|---|---|---|
| 4,599,325 | 7/1986 | Hansen, Jr. et al. | 514/19 |
| 4,658,013 | 4/1987 | Morgan | 530/302 |
| 4,760,180 | 7/1988 | Pitzele et al. | 564/157 |

FOREIGN PATENT DOCUMENTS

| | | | |
|---|---|---|---|
| 0175323 | 3/1986 | European Pat. Off. | C07K 5/00 |
| 2923878 | 1/1981 | Germany | A61K 37/24 |
| 58-75724 | 11/1984 | Japan | C07C 103/52 |
| 59-157961 | 2/1986 | Japan | C07K 5/08 |

*Primary Examiner*—David B. Springer
*Attorney, Agent, or Firm*—Roberta L. Hastreiter; Roger A. Williams

[57] ABSTRACT

The present invention provides substituted tyrosyl diamine amide compounds of general Formula I:

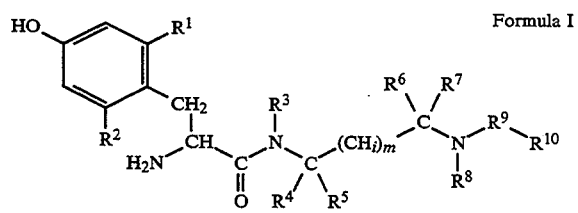

Formula I and the pharmaceutically-acceptable salts thereof, which are useful for inducing analgesia in animals, pharmaceutical compositions comprising a pharmaceutically-acceptable carrier and a compound of Formula I, and a method for inducing analgesia in an animal in need thereof comprising administering a therapeutically-effective amount of a compound of Formula I to the animal.

4 Claims, No Drawings

SUBSTITUTED TYROSYL DIAMINE AMIDE COMPOUNDS

BACKGROUND OF THE INVENTION

1. Field of the Invention

The present invention provides novel compounds having pharmaceutical activity which are useful as pharmaceutical agents and, more particularly, as analgesic agents for the treatment of pain in animals, pharmaceutical compositions containing one or more of these compounds, methods of use employing these compounds and methods of manufacturing these compounds.

More specifically, the present invention concerns: (1) substituted tyrosyl diamine amide compounds which, by apparently acting as neurotransmitters or neuromodulators in the central nervous pain-suppressant system, induce analgesia in animals; (2) pharmaceutical compositions containing one or more of these compounds in combination with a pharmaceutically-acceptable carrier; and (3) methods of treating pain employing these compounds.

Analgesic compounds are agents which alleviate pain without causing a loss of consciousness and, thus, which are useful for treating pain and, often, for reducing inflammation.

The major classes of analgesic compounds include analgesic-antipyretic compounds, which are compounds which alleviate pain and/or reduce fever, such as salicylates, and narcotic analgesics, or opiates, compounds which alleviate pain and/or induce sleep.

While salicylate and salicylate-like agents (non-steroidal antiinflammatory agents or NSAIDS) are efficacious in relieving pain, they often exhibit undesirable side effects, such as gastrointestinal irritation, including bleeding, as with aspirin, allergic response, as with aspirin, and/or liver toxicity with extended use, as with acetaminophen.

The compounds of the present invention are not salicylates, and represent another class of compounds which are useful as analgesic agents.

2. Description of the Related Art

Opioids are a class of drugs which are, to varying degrees, opium-like or morphine-like in their properties. Although opioids are employed therapeutically primarily as analgesics, they have many other pharmacological effects as well, and they have some of the properties of certain naturally-occurring peptides.

By the year 1967, researchers working in the art had concluded that the complex interactions in the body between morphine agonists (morphine-like drugs) and mixed morphine agonist-antagonists could best be explained by postulating the existence of more than one type of cellular receptor for the opioids, and for related drugs.

Subsequent research in the area revealed that multiple categories of opioid receptors exist and, further, that there are at least three distinct families of naturally-occurring opioid peptides: (1) the endorphins; (2) the enkephalins; and (3) the dynorphins.

Although studies concerning the binding of opioid drugs and peptides to specific sites in the brain, and in other organs, have suggested the existence of, perhaps, as many as eight different types of opioid receptors in the body, there is reasonably firm evidence to support the conclusion that three major categories of opioid receptors, designated $\mu$, $\kappa$ and $\delta$, exist in the central nervous system. The classical opioid antagonist, naloxone, has been found to bind with high affinity to all three categories of opioid receptors.

The multiplicity of opioid receptor types in the central nervous system is now well established. Though much work has been directed at defining the structural elements that determine receptor specificity and efficacy, these factors are still, at best, poorly understood.

The rigid alkaloid opiates, typified by morphine, are generally believed to produce analgesia by interacting with the $\mu$ receptor.

It is now well established that the $\delta$ opioid receptor type mediates analgesia in the mouse, and that this site is generally associated with fewer gastrointestinal transit effects, and with less physical dependence, than the $\mu$ opioid receptor type.

In 1975, Hughes and Kosterlitz described the isolation of two naturally-occurring pentapeptides, "methionine enkephalin" ($H_2$N-Tyr-Gly-Gly-Phe-Met-OH) and "leucine enkephalin" ($H_2$N-Tyr-Gly-Gly-Phe-Leu-OH), from the brain. These pentapeptides occur in nerve endings of brain tissue, spinal cord and the gastrointestinal tract, bind to the same receptor sites as do the opiates, and exhibit some weak morphine-like actions, actions which were antagonized by naloxone.

That same year, Goldstein and his colleagues reported the presence of peptide-like substances in the pituitary gland which exhibited opioid activity.

The naturally-occurring pentapeptides isolated by Hughes and Kosterlitz appear to act as neurotransmitters or neuromodulators in the central nervous system, and bind stereospecifically to partially-purified brain opioid receptor sites. See, for example, Bradbury et al., *Nature*, 260, 793 (1976). These natural peptides are also highly active in bioassays for opioid activity, but exhibit only weak, fleeting analgesic activity when injected directly into the brain of the rat, and exhibit no activity when administered systemically in the rodent. See, for example, Belluzzi, et al., *Nature*, 260, 625 (1976).

In an attempt to overcome the lack of in vivo activity of the naturally-occurring pentapeptides isolated by Hughes and Kosterlitz, investigators working in the art have made numerous modifications to these enkephalins.

Among the modifications made to methionine enkephalin has been the synthesis of short-chain, enkephalin-like peptides, among them dipeptide and tripeptide alkylamides, as described by Kiso et al., "Peptide Chemistry 1981," Protein Research Foundation, Osaka, Japan, 65–70 (1982). Vavrek et al., *Peptides*, 2, 303 (1981), disclose analogs of the enkephalins, including the dipeptide, tyrosine-D-alaninephenyl-propylamide.

The large-scale use of synthetic enkephalins has been impractical due to various difficulties. One of the difficulties associated with natural enkephalins is that they are extremely unstable, and their half-lives in the blood are extremely short.

Attempts at solving these problems have focused upon altering the structure of the enkephalin molecule. Alterations in the enkephalin structure produce different pharmacological effects. To some degree, these effects are due to differential interactions with the various opioid receptors. However, it has been difficult to study the role of each receptor type, or to induce selectively the pharmacological and therapeutic effects associated with each receptor type, because the enkephalin analogs, to date, have had a high degree of selectivity for only the mu (μ), rather than for the delta (δ), opioid receptors.

For several years, the prototypic agonist for the δ opioid receptor has been the cyclic enkephalin analog [D-Pen², D-Pen⁵]enkephalin. The recently-discovered deltorphins, heptapeptides of frog skin origin, are also highly selective and potent, in vitro, at this receptor. However, the relatively large size of these peptides suggest potential problems in crossing the blood brain barrier to elicit analgesia after systemic administration, a desirable property for a useful opioid analgesic. This has also hampered attempts to more fully define the functional role of δ receptors in the central nervous system.

Compounds within the present invention are tyrosyl diamine amide opioid agonists which have a substantial affinity for both the μ and the δ opioid receptors, and which produce analgesia following central and peripheral routes of administration in animals.

The compounds of the present invention are structurally distinct from that which has been described in the art.

SUMMARY OF THE INVENTION

The present invention provides compounds having a structure of Formula I:

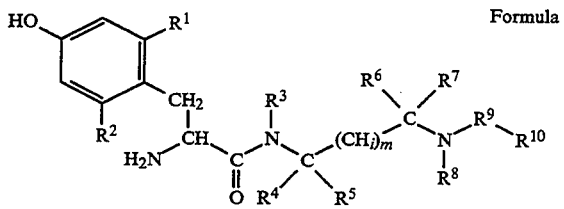

and the pharmaceutically-acceptable salts thereof, wherein:

$R^1$ and $R^2$ are each independently hydrogen, halogen or alkyl having from 1 to 4 carbon atoms;

$R^3$ is hydrogen, or a methyl group which may be taken together with one or more of $R^4$, $R^5$, —(CH$_i$)$_m$—, $R^6$, $R^7$ and $R^8$ to form a single-ring nonaromatic structure;

$R^4$ is hydrogen, alkyl having from 1 to 4 carbon atoms which may be taken together with one or more of $R^3$, $R^5$, —(CH$_i$)$_m$—, $R^6$, $R^7$ and $R^8$ to form a single-ring nonaromatic structure;

$R^5$ is hydrogen, alkyl having from 1 to 4 carbon atoms which may be taken together with one or more of $R^3$, $R^4$, —(CH$_i$)$_m$—, $R^6$, $R^7$ and $R^8$ to form a single-ring nonaromatic structure;

$R^6$ is hydrogen, alkyl having from 1 to 4 carbon atoms which may be taken together with one or more of $R^3$, $R^4$, $R^5$, —(CH$_i$)$_m$—, $R^7$ and $R^8$ to form a single-ring nonaromatic structure;

$R^7$ is hydrogen, alkyl having from 1 to 4 carbon atoms which may be taken together with one or more of $R^3$, $R^4$, $R^5$, —(CH$_i$)$_m$—, $R^6$ and $R^8$ to form a single-ring nonaromatic structure;

$R^8$ is hydrogen or a methyl group which may be taken together with one or more of $R^3$, $R^4$, $R^5$, —(CH$_i$)$_m$—, $R^6$ and $R^7$ to form a single-ring nonaromatic structure;

$R^9$ is —CH$_2$— or

$R^{10}$ is aryl, alkaryl, aminoaryl, aminoalkaryl, alkoxyaryl, alkenylaryl or alkynylaryl;

i is an integer of from 0 to 2; and m is an integer of from 0 to 4.

The present invention also provides pharmaceutical compositions which are pharmaceutically acceptable, and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The symbol "▼" as used herein denotes one of two possible stereoisomers.

The abbreviation "Ac" and the term "acetyl" as used herein mean the group

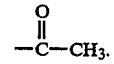

The abbreviation "acyl" as used herein means

The abbreviations "AcOH" and "HOAc" as used herein mean

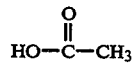

and acetic acid.

The term "alkyl" as used herein means a saturated hydrocarbon radical having from one to ten carbon atoms, within which includes from one to six carbon atoms, and further within which includes from one to three carbon atoms, which can be a straight or branched chain. Representative of such radicals are methyl, ethyl, n-propyl, isopropyl, n-butyl, sec-butyl, isobutyl, tert-butyl, 2-ethylhexyl and the like.

The term "alkaryl" as used herein means an alkyl radical, as defined above, having one or more hydrogen atoms replaced by an aryl radical, as defined below.

The term "alkoxy" as used herein means an alkyl radical, as defined above, having an oxygen atom attached thereto. Representative alkoxy groups include methoxy, ethoxy, n-propoxy, tert-butoxy and the like.

The term "alkoxyaryl" as used herein means an alkoxy radical, as defined above, including an aryl radical, as defined below.

The term "alkenyl" as used herein means a hydrocarbon radical having from one to ten carbon atoms, within which includes from one to five carbon atoms, and further within which includes from one to three carbon atoms, which can be a straight or branched chain, and which contains from one to two —C=C— groups.

The term "alkynyl" as used herein means a hydrocarbon radical having from one to ten carbon atoms, within which includes from one to five carbon atoms, and further within which includes from one to three carbon atoms, which can be a straight or branched chain., and which contains from one to two —C≡C— groups.

The term "alkenylaryl" as used herein means an alkenyl group, as defined above, including an aryl group, as defined below.

The term "alkynylaryl" as used herein means an alkynyl group, as defined above, including an aryl group, as defined below.

The term "amino" as used herein means —NH$_2$.

The term "aminoaryl" as used herein means an amino group, as defined above, having one of its hydrogen atoms replaced by an aryl group, as defined below.

The term "aminoalkaryl" as used herein means an amino group, as defined above, having one of its hydrogen atoms replaced by an alkaryl group, as defined above.

The term "analgesia" as used herein means the reduction, or absence, of sensibility to pain, designating particularly the relief of pain without loss of consciousness.

The term "animal" as used herein includes mammals and non-mammals, and further includes humans and nonhuman mammals.

The term "aryl" and the abbreviation "Ar" as used herein mean unsubstituted, mono- and/or di-substituted 5- and 6-membered single-ring aromatic radicals and/or double-ring aromatic radicals which include from 0 to 4 heteroatoms, and which further include from 0 to 2 heteroatoms. Representative of such radicals are phenyl, pyrimidyl, thienyl, furyl, indolyl, pyrazinyl, isoquinolyl, quinolyl, imidazolyl, pyrrolyl, benzofuryl, benzothienyl, thiophene, pyridinyl, thienyl-pyridinyl, imidazole, thizolyl, oxazole, triazole, tetrazole, pyridinyl-N-oxide and the like.

The abbreviation "Bzl" and the term "benzyl" as used herein means C$_6$H$_5$CH$_2$—.

The phrase "blood brain barrier" as used herein means a chemical barrier made up by the cell walls of the capillaries which are present in the brain tissues, through which drugs circulating in the blood must pass in order to have an effect in the central nervous system.

The abbreviation "Boc" as used herein means t-butyloxycarbonyl.

The phrase "Boc-DMT" as used herein means Boc-2,6-L-dimethyltyrosine.

The abbreviation "C" as used herein means the C or carboxy terminus of an amino acid or peptide or the element carbon, depending upon the context in which it is used, as is known by those of skill in the art.

The term "carbonyl" as used herein means

The term "carboxyl" as used herein means

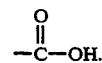

The abbreviation "CH$_2$Cl$_2$" as used herein means methylene chloride.

The term "composition" as used herein means a product which results from the combining of more than one element or ingredient.

The abbreviation "DCC" as used herein means dicyclohexylcarbodiimide.

The abbreviation "DIEA" as used herein means diisopropylethylamine.

The abbreviation "DMF" as used herein means dimethylformamide.

The phrase "ED$_{50}$ value" as used herein means that dose of a compound or drug which produced a biological effect, such as producing analgesia, in 50% of the animals to which the compound or drug was administered.

The abbreviation "Et" as used herein means ethyl (—CH$_2$CH$_3$).

The abbreviation "Et$_2$O" as used herein means diethyl ether.

The term "Et$_3$N" as used herein means triethylamine.

The abbreviation "EtOAc" as used herein means ethyl acetate.

The abbreviation "EtOH" as used herein means ethanol (CH$_3$CH$_2$OH).

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "HOBT" as used herein means 1-hydroxybenzotriazole.

The term "hydroxy" as used herein means —OH.

The abbreviation "IBCF" as used herein means isobutylchloroformate.

The abbreviation "i.g." as used herein means that a compound or drug was administered intragastrically.

The abbreviation "Me" as used herein means methyl (—CH$_3$).

The abbreviation "MeOH" as used herein means methanol (CH$_3$OH).

The abbreviation "N" as used herein means the N or amino terminus of an amino acid or peptide and/or the element nitrogen, depending upon the context in which it is used, as is known by those of skill in the art.

The acronym "NSAID" as used herein means nonsteroidal antiinflammatory drug, as discussed by J. G. Lombardino, Ed. *Nonsteroidal Antiinflammatory Drugs, Chemistry and Pharmacology of Drug Series*, Wiley, New York (1985).

The term "nitro" as used herein means —NO$_2$.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The abbreviation "NMM" as used herein means N-methylmorpholine.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, oxylate, valerate, oleate, palmitate, stearate, laurate, borate, benzoate, lactate, phosphate, tosylate, citrate, maleate, fumarate, succinate, tartrate, napsylate, clavulanate and the like salts and alkali metal salts, such as sodium and potassium, and alkaline earth salts, such as calcium and magnesium.

The abbreviation "Ph" and the term "phenyl" as used herein means the group $C_6H_5$—, derived from benzene.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acyl, acetyl, pivaloyl, t-butyloxycarbonyl (Boc), benzyloxycarbonyl (Cbz), benzoyl and an L- or D-aminoacyl residue, which may itself be N-protected similarly.

The abbreviation "PTS" as used herein means p-toluene-sulfonic acid.

The abbreviation "RaNi" as used herein means Raney nickel.

The abbreviation "s.c." as used herein means that a compound or drug was administered subcutaneously.

The phrase "a single-ring nonaromatic structure" means a 5- and/or 6-membered nonaromatic single-ring structure which includes from 0 to 4 heteroatoms, and which further includes from 0 to 2 heteroatoms.

The phrases "systemic administration" and "peripheral administration" as used herein mean the administration of a compound, drug or other material other than directly into the central nervous system, such that it enters the patient's system and, thus, is subject to metabolism and other like processes, for example, subcutaneous administration.

The abbreviation "TEAP" as used herein means triethylamine-phosphate buffer.

The abbreviation "TFA" as used herein means trifluoroacetic acid.

The phrase "therapeutically-effective amount" as used herein means that amount of a compound, material, or composition which is effective for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product," "title peptide" and "title material" as used herein mean that compound, product, peptide or material whose chemical name is given, and whose structure is shown, in the particular example, or subpart thereof, referred to. If no particular example, or subpart thereof, is referred to, it means that compound, product, peptide or material whose chemical name is given, and whose structure is shown, in the particular example, or subpart thereof, in which it appears.

The phrase "Z group" and the letter "Z" as used herein mean a benzyloxylcarbonyl group.

Amino acids appearing herein may be identified according to the following three-letter abbreviations.

| Amino Acid | Three-Letter Abbreviation |
| --- | --- |
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Histidine | His |
| Isoleucine | Ile |
| Leucine | Leu |
| Lysine | Lys |
| Methionine | Met |
| Penicillamine | Pen |
| Phenylalanine | Phe |
| Proline | Pro |
| Serine | Ser |
| Threonine | Thr |
| Tryptophan | Trp |
| Tyrosine | Tyr |

| Amino Acid | Three-Letter Abbreviation |
|---|---|
| Valine | Val |

The letters "L" and "D" appearing herein indicate whether a particular amino acid has the naturally-occurring configuration (L) or has the nonnaturally occurring configuration (D). Unless otherwise indicated, such as in the names or the structures for the various compounds appearing herein, the amino acids appearing herein are L-enantiomorphs, rather than D-enantiomorphs.

(2) Description of Invention

In one aspect, the present invention provides compounds comprising a structure of Formula I, as described above in the "Summary of Invention" section, which are pharmaceutically acceptable, and pharmaceutically-acceptable salts thereof.

As is illustrated directly below, the compounds of the present invention comprise a class of substituted tyrosyl diamine amide compounds which contain: (1) a tyrosine, or modified tyrosine, amino acid residue; (2) a diamine spacer unit located between a tyrosine, or modified tyrosine, amino acid residue and a unit which contains an aromatic ring (aryl group) (an aromatic containing unit); and (3) a unit which contains an aromatic ring.

Tyrosyl Diamine Amide Compounds of the Invention

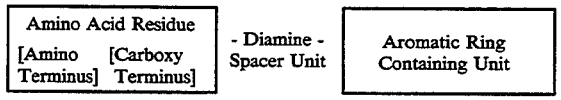

The diamine spacer arm which links the tyrosine, or modified tyrosine, amino acid residue to the aromatic ring containing unit contains two —NH groups, which may be connected directly together to form an —NH—NH— group, or which may include straight- or branched-chain alkyl radicals between the two nitrogen atoms, preferably having from 1 to 4 carbon atoms. For example, the compound described in Example 6 has the following diamine spacer arm:

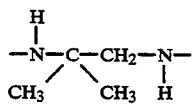

Preferably, the diamine spacer arm contains the two nitrogen atoms separated by a —CH$_2$—CH$_2$— group.

Preferred compounds of the present invention are those in which the R$^1$ and R$^2$ positions thereof, as shown in Formula I, are each methyl. The most preferred compounds of the present invention are the compounds shown and described in Examples 6 and 13.

Specific compounds contemplated as falling within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans- geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66:1–19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. As described in detail below, the pharmaceutical compositions of the present invention may be specially formulated for oral administration in solid or liquid form, for parenteral injection, or for rectal or vaginal administration.

In yet a further aspect, the present invention provides a method for eliminating or ameliorating pain in an animal comprising administering a therapeutically-effective amount of a compound of Formula I, as described hereinabove, to the animal.

(3) Utility

By virtue of their analgesic activity, the compounds of the present invention, and the pharmaceutical compositions comprising one or more of these compounds, are useful as analgesic agents for the elimination or amelioration of pain in animals.

(4) Methods of Preparation

In general, the compounds of the present invention may be prepared by the methods illustrated in the following general reaction schemes, or by modifications thereof, using readily available starting materials, reagents and conventional synthetic procedures. In these reactions, it is also possible to make use of variants which are in themselves known, but are not mentioned here.

Unless otherwise specified, the various substituents of the compounds shown in the general reaction schemes are defined in the same manner as they are defined above in Formula I in the "Summary of Invention" section.

If a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, a substituted or unsubstituted diamine is reacted with one equivalent of para-toluene-sulfonic acid and one equivalent of benzyloxy chloroformate. The resulting mono N-benzyloxycarbonyl protected diamine is treated with an 'activated' N-Boc protected α-amino acid. The two methods of amino acid activation used are: (1) Mixed Anhydride Coupling, which involves treatment of the acid with one equivalent each of N-methyl-morpholine and isobutylchloroformate, and which is known by those of skill in the art; and (2) Carbodiimide Coupling, which involves treatment of the acid with the appropriate amine, dicyclohexylcarbodiimide and hydroxybenzotriazole, and which is also known by those of skill in the art. The product of this reaction is either treated with acid to remove the Boc protecting group or treated with hydrogen in the presence of palladium on carbon to give Compound A. Compound A is also obtained in one step by the coupling of the N-Boc protected α-amino acid with an unprotected diamine in the presence of one equivalent of para-toluenesulfonic acid. The amino groups in Compound A are suitably functionalized as is outlined in this scheme, and as is illustrated in the examples presented hereinbelow, to give a variety of compounds. Thus, for example, treatment of the amines with isocyanates gave urea-type compounds, and treatment of the amines with activated acids gave amide-type compounds. The resulting products of these functionalization reactions are treated with acid to provide the salts of the diamides.

General Reaction Scheme No. 2 outlines alternative and complementary procedures used for obtaining compounds of this invention. Thus, in this scheme, a diamine is coupled to N-Boc protected α-amino acids using a Carbodiimide Coupling Procedure or Mixed Anhydride Coupling Procedure. When $R^9$-$R^{10}$ represent a benzyl group, the products are treated with acid to give the salts of the target diamides. When $R^9$-$R^{10}$ represent a benzyloxycarbonyl group, the products are hydrogenolysed to give a free amine which are treated in the same manner as is Compound A in General Reaction Scheme No. 1.

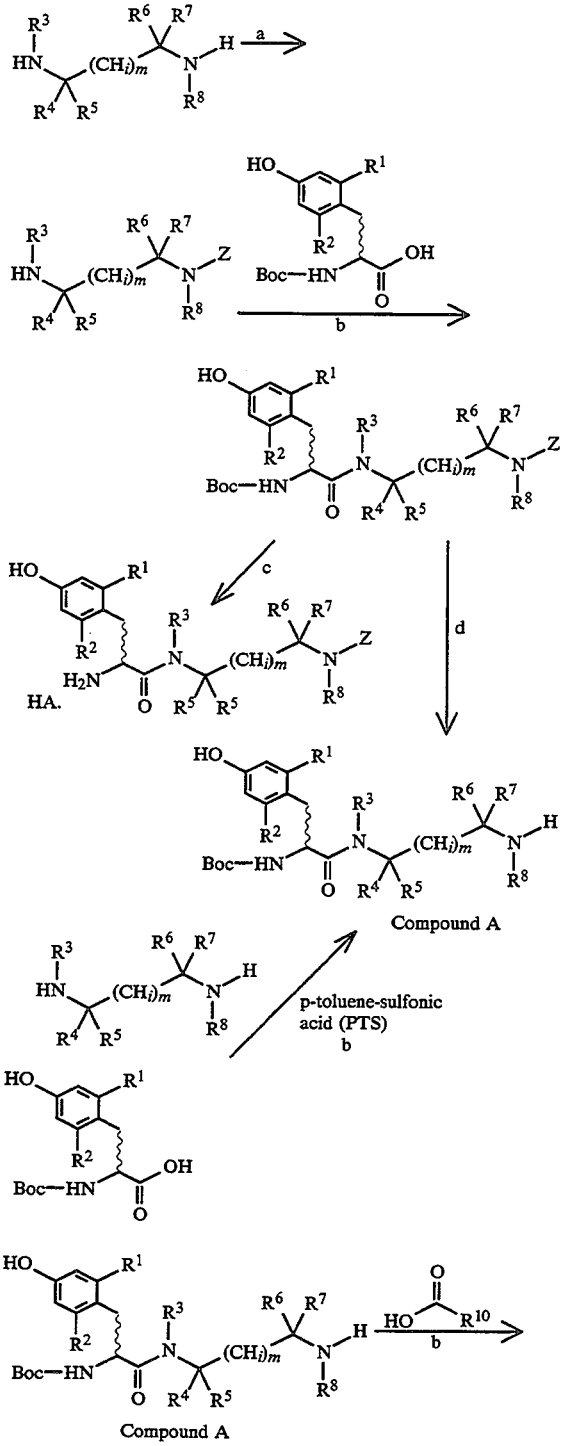

-continued
GENERAL REACTION SCHEME NO. 1

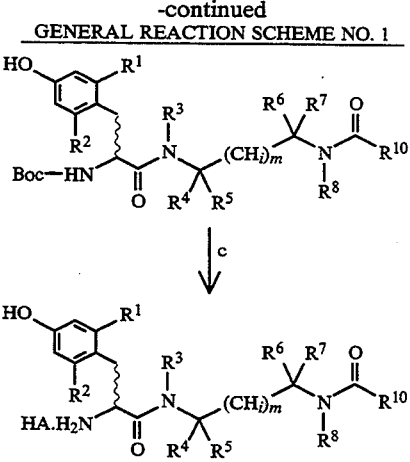

The following letters correspond to the same letters employed in General Reaction Scheme No. 1:

(a) One equivalent each of para-toluenesulfonic acid and benzyloxychloroformate.
(b) Isobutyl chloroformate, N-methylmorpholine (Mixed Anhydride Coupling) or dicyclohexyl carbodiimide and hydrobenzotriazole (Carbodiimide Coupling).
(c) HCl in dioxane-Acetic Acid or HCl in dioxane-$CH_2Cl_2$.
(d) Hydrogen-Palladium on Carbon.

GENERAL REACTION SCHEME NO. 2

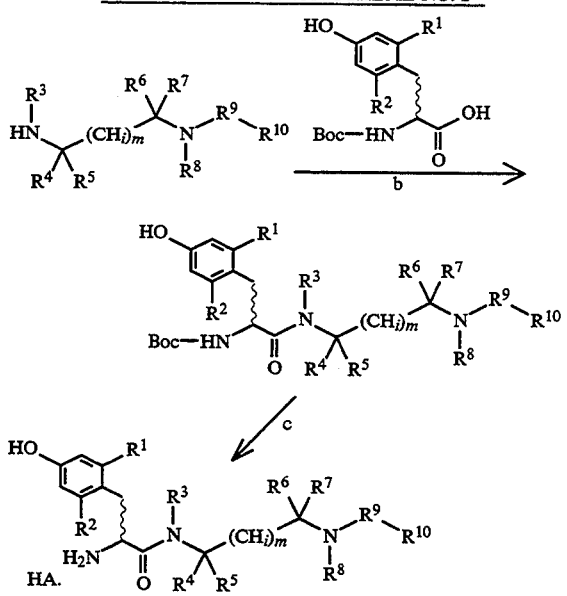

The following letters correspond to the same letters employed in General Reaction Scheme No. 2:

(b) Isobutyl chloroformate, N-methylmorpholine (Mixed Anhydride Coupling) or dicyclohexyl carbodiimide and hydroxybenzotriazole (Carbodiimide Coupling).
(c) HCl in dioxane-Acetic Acid or HCl in dioxane-$CH_2Cl_2$.

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful for treating pain in animals. A physician or veterinarian of ordinary skill in the art can readily determine whether or not a patient is in pain.

The pharmaceutical compositions of the present invention, which will typically comprise one or more of the compounds of Formula I, as described in the "Summary of Invention" section, as an active ingredient in a mixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are oral, subcutaneous, and intravenous, the most preferred mode of administration is subcutaneous.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alphatocopherol, and the like; and (3) metal chelating agents, such as citric acid, ethylenediaminetetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the abovedescribed excipients.

Liquid dosage forms for oral administration of the compounds of the invention include pharmaceutically acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following non-limiting examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

All patents and publications referred to in the examples, and throughout the specification, are hereby incorporated herein by reference, without admission that such is prior art.

In the examples, all parts are by weight, and all temperatures are degrees Celsius, unless otherwise noted. Unless otherwise noted, Infrared (IR) and Nuclear Magnetic Resonance (NMR) spectra were consistent with the assigned structure.

Unless otherwise indicated, all of the equipment employed in the examples is commercially available.

All starting materials used in the examples are commercially available, and were obtained from Aldrich Chemical Co. (Milwaukee, Wis.), TCI American Tokyo (Portland, Oreg.), Advanced Chemtech (Louisville, Ky.), Fluka Chemical Corp. (Ronkonkoma, N.Y.), Bachem Bioscience Inc. (Philadelphia, Pa.), Chemical Dynamics Corp. (South Plainfield, N.J.), Sigma Chemical Co. (St. Louis, Mo.) and/or Peptides International (Louisville, Ky.).

While Examples 1–22 describe specific methods for synthesis of compounds within the present invention, Examples 23–24 describe two different assays which were conducted with compounds of the present invention.

Example 1

Phenylmethyl(2-amino-2-methylpropyl)carbamate

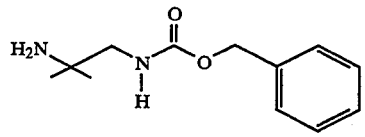

A solution of benzyloxychloroformate (3.9 g) in toluene (15 mL) was added dropwise to a stirred solution of 1,2-diamino-2-methylpropane (5 g) in toluene (90 mL) at 0° C. for 20 minutes. After 40 hours, the reaction mixture was filtered. The filtrate was concentrated in vacuo. The residue was redissolved in toluene and stripped of all solvent several times. The residue was dried in vacuo to give the title compound as a white solid (4.3 g), which was used in Example 2 without further purification.

Example 2

Phenylmethyl[2-[[2S-[[(1,1-dimethylethoxy)carbonyl-]amino]-3-(4-hydroxy-2,6-dimethylphenyl)-1-oxopropyl]amino]-2-methylpropyl]carbamate

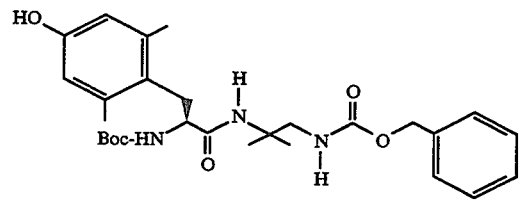

To a stirred solution of Boc-2,6-L-dimethyltyrosine (Boc-DMT, 13.9 g) in methylene chloride ($CH_2Cl_2$, 600 mL) at −78° C. was added N-methylmorpholine (NMM, 4.9 mL) followed by isobutylchloroformate (IBCF, 6.1 mL). The mixture was allowed to warm to 0° C. over 25 minutes and was then recooled to −78° C. To this was added the title compound of Example 1 (10 g), and stirring was continued for 48 hours. The mixture was concentrated in vacuo. The residue was dissolved in ethyl acetate (EtOAc), washed with 0.5N $KHSO_4$, dried over $Na_2SO_4$, and concentrated in vacuo. The residue was purified by chromatography over silica gel using 5% ethanol in 8:11 $CH_2Cl_2$/n-hexane as eluant to give 8.9 g of the title compound as a white solid.

Example 3

Phenylmethyl[2-[[2S-amino-3-(4-hydroxy-2,6-dimethylphenyl)-1-oxopropyl]amino]-2-methylpropyl]carbamate, monohydrochloride

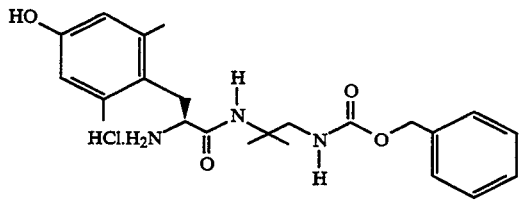

The title compound of Example 2 (0.4 g) was dissolved in 10 mL of acetic acid (HOAc) and 1.2 mL of 7N hydrogen chloride (7N HCl) in dioxane. The resulting solution was allowed to stir at room temperature for 30 minutes. The volatiles were removed in vacuo. The residue was triturated with diethyl ether (Et$_2$O), filtered and dried in vacuo to give the title compound as a white solid.

Calculated for C$_{23}$H$_{32}$N$_3$O$_4$+0.4 H$_2$O+HCl (MW=457.18): C, 60.43; H, 7.23;N, 9.19; Cl, 7.75.

Found: C, 60.45; H, 7.22;N, 8.86; Cl, 7.67.

[α]$_D$= +69.5°, MeOH.

Example 4

Compound A 1,1-Dimethylethyl[1S-[[(2-amino-1,1-dimethylethyl)amino]carbonyl]-2-(4-hydroxy-2,6-dimethylphenyl)ethyl]carbamate

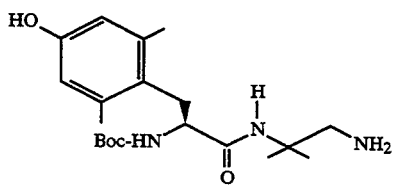

Compound B 1,1-Dimethylethyl[2-[(2-amino-2-methylpropyl)amino]-1S-[(4-hydroxy-2,6-dimethylphenyl)methyl]-2-oxoethyl]carbamate

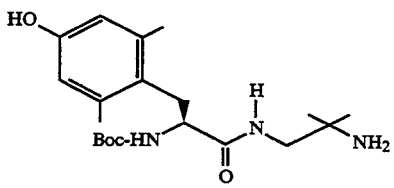

The title compound of Example 2 (6.07 g) was subjected to hydrogenation in a standard Parr apparatus in 100 mL of methanol (MeOH) with 4% Pd on carbon under 5 psi hydrogen for 16 hours. The mixture was filtered to remove the catalyst. The filtrate was concentrated to dryness to leave 4.3 g of a mixture of the title compounds as white solids.

Example 5

1,1-Dimethylethyl[1S-[[[1,1-dimethyl-2-[(2quinolinylcarbonyl)amino]ethyl]amino]carbonyl]-2-(4-hydroxy-2,6-dimethylphenyl)ethyl]carbamate

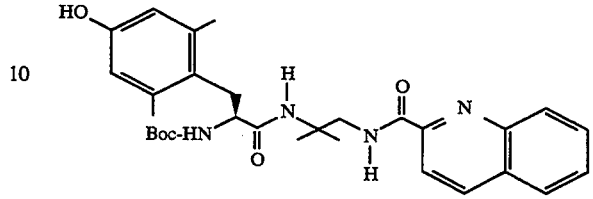

The title Compounds A of Example 4 (1.0 g) were coupled to quinaldic acid (460 mg) using the mixed anhydride coupling method as described in Example 2 above. The crude product was chromatographed over silica gel. The title compound was isolated as a white solid.

Example 6

N-[2-[[2S-amino-3-(4-hydroxy-2,6-dimethylphenyl)-1-oxopropyl]amino]-2-methylpropyl]-2-quinolinecarboxamide, hydrochloride

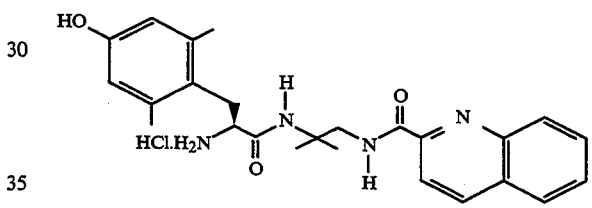

The title compound of Example 5 (420 mg) was treated with 6.9N HCl in dioxane (1.1 mL) by the procedure of Example 3 to provide the title compound as a white solid.

Calculated for: C$_{25}$H$_{30}$N$_4$O$_3$+3H$_2$O+1.7 HCl (MW=550.55) C, 54.54; H, 6.90;N, 10.18; Cl, 10.95.

Found: C, 54.46; H, 6.03;N, 9.49; Cl, 11.05.

[α]$_D$= +94.7°, MeOH.

H$^1$NMR (CD$_3$OD) δ: 1.13 (s, 3H), 1.38 (s, 3H), 2.3 (s, 6H).

Example 7

1,1-Dimethylethyl[1S-[[[1,1-dimethyl-2-[(3-quinolinylcarbonyl)-amino]ethyl]amino]carbonyl]-2-(4-hydroxy-2,6-dimethylphenyl)ethyl]carbamate

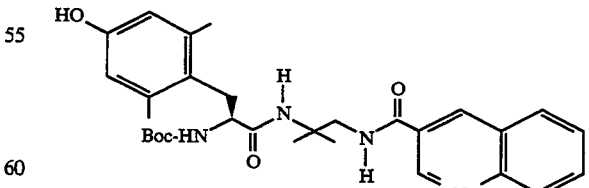

The title Compound A of Example 4 (1.0 g) was coupled to 3-quinoline carboxylic acid (460 mg) using the mixed anhydride coupling method as described in Example 2 above. The crude product was chromatographed over silica gel to give the title compound as a white solid.

Example 8

N-[2-[[2S-amino-3-(4-hydroxy-2,6-dimethylphenyl)-1-oxopropyl]amino]-2-methylpropyl]-3-quinolinecarboxamide, hydrochloride

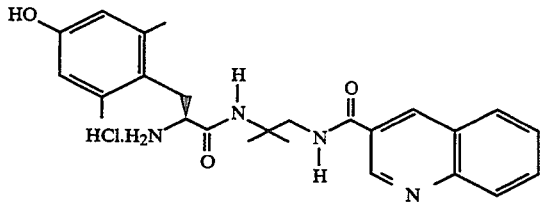

The title compound of Example 7 (250 mg) was treated with 6.9N HCl in dioxane (0.7 mL) by the procedure of Example 3 to give the title compound as a white solid.

Calculated for $C_{25}H_{30}N_4O_3 + 0.75$ $H_2O + 1.8$ HCl (MW=513.69): C, 58.48; H, 6.53;N, 10.91; Cl, 12.42.

Found: C, 58.36; H, 6.64;N, 10.34; Cl, 12.50.

$[\alpha]_D = +34.4°$, MeOH.

H¹NMR (CD₃OD) δ: 1.11 (s, 3H), 1.4 (s, 3H), 2.3 (s, 6H).

Example 9

Compound A:

1,1-Dimethylethyl[1S-[[[1,1-dimethyl-2[[[(phenylmethyl)amino]carbonyl]amino]ethyl]amino]carbonyl]-2-(4-hydroxy-2,6-dimethylphenyl)ethyl]carbamate

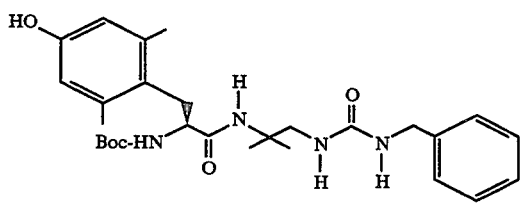

Compound B:

1,1-Dimethylethyl[2-(4-hydroxy-2,6-dimethylphenyl)-1S[[[2methyl]2[[[(phenylmethyl)amino]carbonyl]amino]propyl]amino]carbonyl]ethyl]carbamate

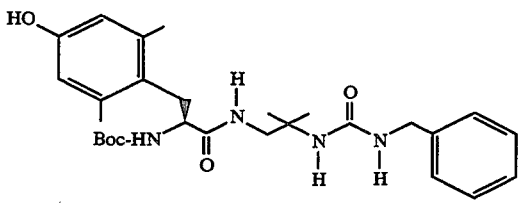

The mixture of the two title compounds of Example 4 (1.0 g) was stirred with benzylisocyanate in a mixture of benzene (25 mL) and CH₂Cl₂ (15 mL) for 18 hours at room temperature. The reaction mixture was washed with 0.5N KHSO₄, dried over MgSO₄ and concentrated in vacuo. The residue was chromatographed to give Compound A (0.18 g) as the more polar component and Compound B (0.29 g) as the less polar component.

Compound A

Calculated for $C_{28}H_{40}N_4O_5 + 0.5$ H₂O (MW=521.66): C, 64.47; H, 7.92;N, 10.34.

Found: C, 64.62; H, 7.94;N, 10.34.

$[\alpha]_D = +33.1°$, CHCl₃.

Compound B

Calculated for $C_{28}H_{40}N_4O_5 + 0.5$ H₂O (MW=521.66): C, 64.47; H, 7.92;N, 10.34.

Found: C, 64.82; H, 7.94;N, 10.33. $[\alpha]_D = +15.4°$, CHCl₃.

Example 10

αS-amino-N-[1,1-dimethyl-2-[[[(phenylmethyl)amino]carbonyl]amino]ethyl]-4-hydroxy.2,6-dimethylbenzenepropanamide, hydrochloride

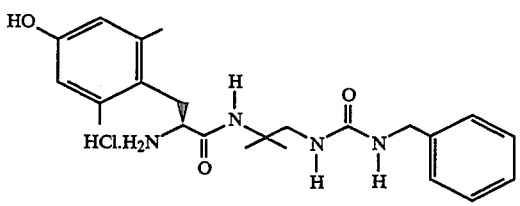

The title Compound A of Example 9 (133 mg) was treated with 6.9N HCl in dioxane (0.6 mL) by the procedure of Example 3 to give the title compound as a white solid (102 mg).

Calculated for $C_{23}H_{32}N_4O_3 + 1.4$ HCl + 0.75 H₂O (MW=477.09): C, 57.90; H, 7.37;N, 11.74; Cl, 10.40.

Found: C, 57.71; H, 7.19;N, 11.37; Cl, 10.60.

$[\alpha]_D = +42.9°$, MeOH.

H¹NMR (CD₃OD) δ:1.01 (s, 3H), 1.25 (s, 3H), 2.27 (s, 6H)

Example 11

αS-amino-4-hydroxy-2,6-dimethyl-N-[2-methyl-2-[[[(phenylmethyl)amino]carbonyl]amino]propyl]benzenepropanamide, hydrochloride

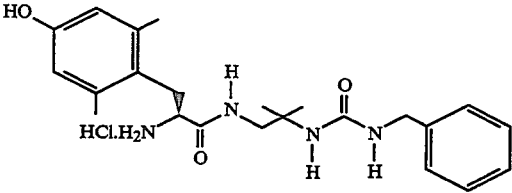

The title Compound B of Example 9 (241 mg) was treated with 6.9N HCl in dioxane (1.0 mL) by the procedure of Example 3 to give the title compound as a white solid (190 mg).

Calculated for $C_{23}H_{32}N_4O_3 + 1.2$ HCl + 0.75 H₂O (MW=469.80): C, 58.80; H, 7.45;N, 11.93; Cl, 9.06.

Found: C, 58.94; H, 7.39;N, 11.65; Cl, 10.36.

$[\alpha]_D = +55.6°$, MeOH.

H¹NMR (CD₃OD) δ: 1.02 (s, 3H), 1.13 (s, 3H), 2.26 (s, 6H).

Example 12

Compound A 1,1-Dimethylethyl[1S-[[[1,1-dimethyl-2-[(1-oxo-3-phenylpropyl)amino]ethyl]amino]carbonyl]-2-(4-hydroxy-2,6-dimethylphenyl)ethyl]carbamate

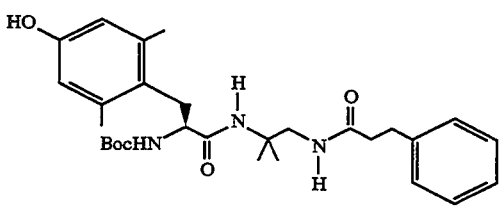

Compound B 1,1-Dimethylethyl[1S-[[[2-methyl-2-[(1-oxo-3-phenylpropyl)amino]ethyl]amino]carbonyl]-2-(4-hydroxy-2,6-dimethylphenyl)ethyl]carbamate

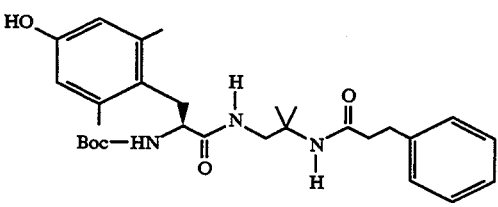

The mixture of the title compounds of Example 4 (1.5 g, 3.95 mmol) was coupled to hydrocinnamic acid (586 mg, 3.90 mmol) using the mixed anhydride procedure as described in the Example 2 to give a mixture of the more polar title Compound A (220 mg) and the less polar title Compound B (556 mg) as white solids. Both of the isomers were separated by chromatography.

Compound A

Calculated for $C_{29}H_{41}N_3O_5 + 0.25$ $H_2O$ (MW=516.17): C, 67.48; H, 8.10;N, 7.86.
Found: C, 67.16; H, 8.22;N, 7.86.
$[\alpha]_D = +41.2°$, $CHCl_3$.

Compound B

Calculated for $C_{29}H_{41}N_3O_5 + 0.25$ $H_2O$ (MW=516.17): C, 67.48; H, 8.10;N, 7.86.
Found: C, 67.37; H, 8.23;N, 8.03.
$[\alpha]_D = +20.0°$, $CHCl_3$.

Example 13

αS-amino-N-[1,1-dimethyl-2-[(1-oxo-3-phenylpropyl)amino]ethyl]-4-hydroxy-2,6-dimethylbenzenepropanamide, hydrochloride

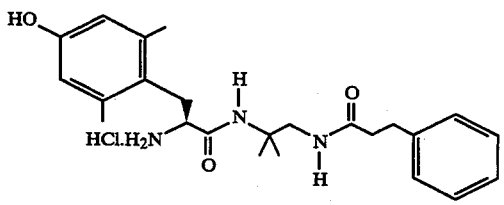

The title Compound A of Example 12 (137 mg) was treated with 6.9N HCl in dioxane (0.6 mL) by the procedure of Example 3 to give the title compound as a white solid (107 mg).

Calculated for $C_{24}H_{33}N_3O_3 + 1.1$ HCl + 0.33 $H_2O$ (MW=457.60): C, 62.99; H, 7.66;N, 9.18; Cl, 8.52.
Found: C, 62.85; H, 7.67;N, 8.89; Cl, 8.34.
$[\alpha]_D = +50.9°$, MeOH.

$H^1$NMR ($CD_3OD$) δ: 0.97 (s, 3H), 1.17 (s, 3H), 2.28 (s, 6H).

Example 14

αS-Amino-4-hydroxy-2,6-dimethyl-N-[2-methyl-2-[(1-oxo-3-phenylpropyl)amino]propyl]benzenepropanamide, hydrochloride

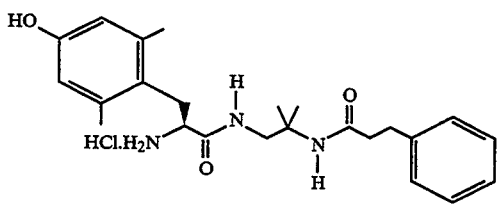

The title Compound B of Example 12 (464 mg) was treated with 6.9N HCl in dioxane (2.0 mL) by the procedure of Example 3 to provide the title compound as a white solid salt (384 mg).

Calculated for $C_{24}H_{33}N_3O_3 + 1.1$ HCl + 0.33 $H_2O$ (MW=457.60): C, 62.99; H, 7.66;N, 9.18; Cl, 8.52.
Found: C, 62.96; H, 7.66;N, 9.04; Cl, 8.27.
$[\alpha]_D = +84.6°$, MeOH.

$H^1$NMR ($CD_3OD$) δ: 1.01 (s, 3H), 1.08 (s, 3H), 2.26 (s, 6H).

Example 15

1-[2S-Amino-3-(4-hydroxy-2,6-dimethylphenyl)-1-oxopropyl]-4-(phenylmethyl)piperazine, dihydrochloride

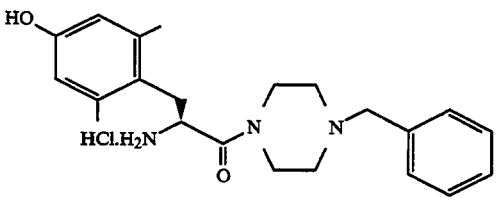

To a solution of 2 g of Boc-DMT in 25 mL of THF at −23° C. was added 0.71 mL of NMM followed by 0.84 mL of IBCF. The mixture was stirred for 30 minutes. To this was added a solution of 1.13 mL of N-benzylpiperazine in 5 mL of THF. The mixture was stirred for 16 hours and concentrated in vacuo. The residue was taken up in EtOAc and water. The organic phase was washed with saturated $Na_2CO_3$, dried over $MgSO_4$ and concentrated in vacuo. The residue was chromatographed on silica gel using 60% EtOAc in hexane containing 2% triethylamine to give 3 g of a white solid (Compound A, the Boc precursor of the title compound). 0.2 g of this solid was dissolved in a mixture of 5 mL each of $CH_2Cl_2$ and 7N HCl in dioxane. The solution was allowed to stand at room temperature for 15 minutes. The volatiles were removed in vacuo to give the title compound as a white solid.

HPLC (Zorbax-Rx—C-8, 30/70 to 90/10 for 20 minutes, 90/10 for 5 minutes, methanol/TEAP) =11.21

Example 16

αS-amino-4-hydroxy-2,6-dimethyl-N,[1-phenylmethyl)-3-pyrrolidinyl]-benzenepropaneamide, dihydrochloride

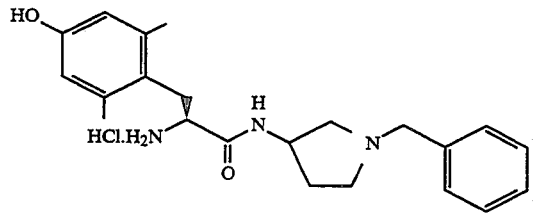

1-Benzyl-3-amino-pyrrolidine was used in the place of 1-benzylpiperazine in the mixed anhydride procedure of Example 15 to give the title compound hydrochloride salt.

Example 17

1,1-Dimethylethyl- [2-[[1,1-dimethyl-2-[(1-oxo-3-phenyl-2-propynyl)amino]ethyl]amino]-1S-[(4-hydroxy-2,6-dimethylphenyl)methyl]-2-oxoethyl]carbamate

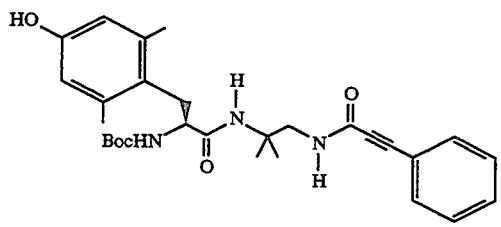

The mixture of the title compounds of Example 4 (800 mg) was coupled to phenylpropiolic acid (384 mg) using the mixed anhydride procedure described in Example 2 to give a mixture of compounds from which the title compound (450 mg) was isolated by chromatography.

Calculated for $C_{24}H_{29}N_3O_3$ (MW=407.514) C, 66.27; H, 7.48;N, 7.99.

Found: C, 66.27; H, 7.24;N, 7.85.

$[\alpha]_D = +724°$ (MeOH)

Example 18

S-Amino-N-[1,1-dimethyl-2-[(1-oxo-3-phenyl-2-propynyl)amino]ethyl]-4-hydroxy-2,6-dimethylbenzenepropanamide, monohydrochloride

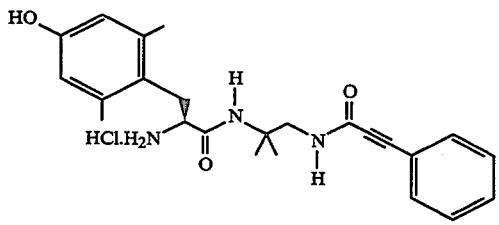

The title compound of Example 17 (450 mg) was treated with 6.9N HCl in dioxane (0.6 mL) by the procedure described in Example 3 to give the title compound as a white solid.

Calculated for $C_{24}H_{29}N_3O_3 + 1.25$ HCl+0.5 AcOH+1.0 H$_2$O (MW =501,132): C, 59.92; H, 6.89;N, 8.38; Cl, 8.84. Found: C, 59.79; H, 6.63;N, 8.35; Cl, 8.89.

$[\alpha]_D = +62.3°$, MeOH.

H$^1$NMR (CD$_3$CO$_2$D) d: 0.9 (s, 3H), 1.3 (s, 3H), 2.3 (s, 6H).

Example 19

Compound A 2,2-dimethylethyl-[2-[[1,1-dimethyl-2-[(1-oxo-3-phenyl-2-propenyl)amino]ethyl]amino]-1S-[(4-hydroxy-2,6-dimethylphenyl)methyl]-2-oxoethyl]carbamate

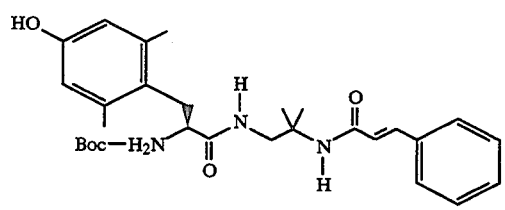

Compound B 1,1-dimethylethyl-[2-[[1,1-dimethyl-2-[(1-oxo-3-phenyl-2-propenyl)amino]ethyl]amino]-1S-[(4-hydroxy-2,6-dimethylphenyl)methyl]-2-oxoethyl]-carbamate

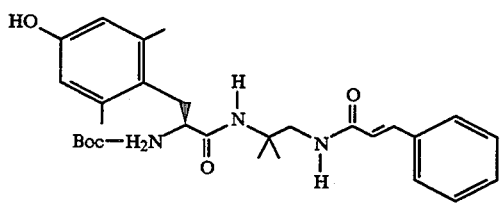

The mixture of the title compounds of Example 4 (1.0 g) was coupled to a t-cinnamic acid (390 mg) using the mixed anhydride procedure as described in Example 2 to give a mixture of compounds from which the title compound mixture of 80% Compound A and 20% Compound B was isolated by chromatography.

Analysis Calculated for $C_{24}H_{31}N_3O_3 + H_2O$ (MW =444.983): C, 66.01; H, 7.83;N, 7.96.

Found: C, 66.23; H, 7.72;N, 7.83.

Example 20

Compound A

S-amino-N-[2,2-dimethyl-2=[(1-oxo-3-phenyl-2-propenyl)amino]ethyl]-4-hydroxy-2,6-dimethylbenzenepropanamide, monohydrochloride

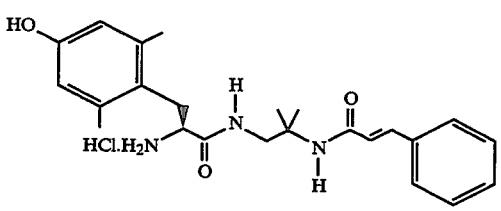

Compound B

S-amino-N-[1,1-dimethyl-2-[(1-oxo-3-phenyl-2-propenyl)amino]ethyl]-4-hydroxy-2,6-dimethylbenzenepropanamide, monohydrochloride

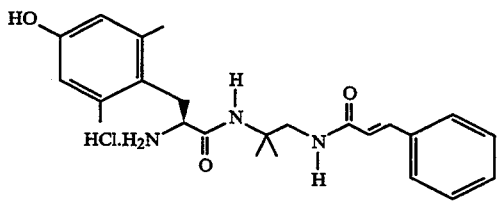

The title compound of Example 17 (650 mg) was treated with 6.9N HCl in dioxane by the procedure of Example 3 to give the title mixture of 80% Compound A and 20% Compound B as a white solid (500 mg).

Analysis Calculated for $C_{24}H_{31}N_3O_3+HCl+1.25 H_2O$ (MW =468.51): C, 61.53; H, 7.42;N, 8.97; Cl, 7.57. Found: C, 61.53; H, 7.12;N, 8.84; Cl, 7.79.

Example 21

Phenylmethyl[2-[[2S-[[(1,1-dimethylethoxy)carbonyl]amino]-3-(4-hydroxy-2,6-dichlorophenyl)-1-oxopropyl]-amino]-2-methylpropyl]carbamate

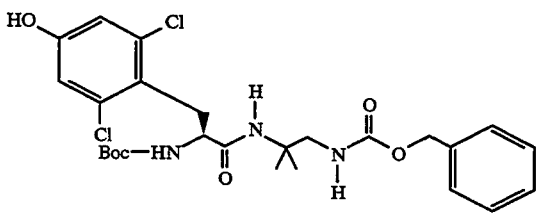

The title compound is synthesized by coupling Boc-2,6-L-dichlorotyrosine to the title compound of Example 1 by the method described in Example 2.

Example 22

Phenylmethyl[2-[[2S-amino-3-(4-hydroxy-2,6-dichlorophenyl)-1-oxopropyl]-amino]-2-methylpropyl]carbamate, monohydrochloride

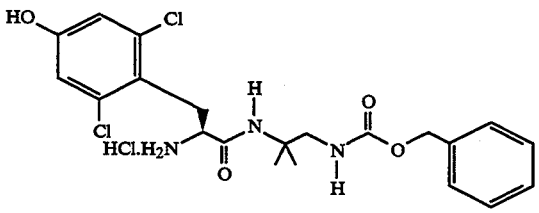

The title compound of Example 21 is treated with HCl in dioxane by the procedure described in Example 3 to give the title compound.

Example 23

Writhing Assay

The "Writhing Assay" is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. Exp. Ther.*, 153,400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds within the present invention exhibit analgesic activity in mice, as shown by the results of the Writhing Assay presented in Table I below.

This assay was conducted generally in the manner described by R. I. Taber, "Predictive Value of Analgesic Assays in Mice and Rats," *Advances in Biochemical Psychopharmacology*, 8, 191 (1974).

Two hundred CD Charles River mice, weighing 20 to 30 grams, were used in this assay.

Twenty-five minutes after subcutaneous administration to the mice of 10 mg per kilogram (mpk) of body weight of a tyrosyl diamine amide compound of the invention (hereinafter "test compound"), 0.1 mL per 10 g of body weight of a 0.025% w/v solution of phenylbenzoquinone (PBQ) was injected intraperitoneally into each mouse. Some mice were given saline in place of a test compound, and were used as a control group.

Five minutes later, each mouse was individually placed into a glass beaker for observation, and the number of writhes occurring during the following ten-minute period was counted.

A compound was considered to be "active" (to have produced analgesia in a mouse) if, after the administration of 10 mg per kilogram (mpk) of body weight of the compound to the mouse, the number of writhes elicited by a mouse injected with PBQ was equal to, or less than, one-half the median number of writhes recorded for the saline-treated control group of mice that day, as described by R. I. Taber, supra.

The standard initial screening dose of a test compound employed in this assay was 10 mpk per gram of body weight. If this initial screening dose of the compound produced analgesia in seven of ten mice, then the effect of additional doses of the compound on the writhing response was evaluated, and then the $ED_{50}$ value (that dose of a compound which produced analgesia in 50% of the mice to which the compound was administered) was calculated. A maximum likelihood function was used to determine the ED50 value. (The slopes of the dose-response curves for the compounds analyzed were compared as described by Tallarida and Murray, *Manual of Pharmacologic Calculations*, Page 11 (Springer Verlag, New York, 1981)).

The results for the compounds analyzed in this assay, and discussed in the examples which correspond thereto, are presented in Table I below, and are expressed in terms of both the number of mice out of ten in which a compound was determined to be active and the $ED_{50}$ value. Each of the compounds of the present invention tested in this assay was found to be active in all ten of the mice to which the compound was administered when administered subcutaneously at a dose of 10 mpk.

As Table I shows, the tyrosyl diamine amide compounds of the invention shown and synthesized in Examples 6 and 13 were determined to be the most potent compounds of the invention tested in the Writhing Assay, and are the most preferred compounds of the invention.

TABLE I

Data Generated from the Wrathing Assay

| Compound Tested | Subcutaneous (S.C.) Number of Animals out of 10 Exhibiting Analgesia or $ED_{50}$ |
|---|---|
| Example 6 | 10/10 (5 mpk) |
| Example 13 | 10/10 (5 mpk) |

Example 24

Opiate Binding Assay

Compounds within the present invention were also evaluated in an opioid radioligand binding assay, which measures the affinity of opioids for specific opioid receptors in rat forebrain, by their ability to displace the binding of radiolabeled ligands specifically bound to $\mu$ and/or $\delta$ opioid receptors isolated from rat brain. Compounds which are determined to be active in this in vitro assay will generally have opioid-like effects in animals, including analgesia, unless they are not bioavailable.

A purified homogenate of receptor membranes was prepared from the brains of the rats according to the method described by K. J. Chang et al., "Multiple Opiate Receptors: Enkephalins and Morphine Bind to Receptors of Different Specitivity," *J. Biol. Chem.*, 254, 2610–2618 (1979).

Male Charles River Sprague-Dawley albino rats weighing 150 to 300 g were stunned and decapitated. Their forebrains (minus the cerebellum and associated hindbrain) were quickly removed and rinsed in ice-cold 50 mM Tris buffer, pH 7.4, and homogenized in 20 volumes of buffer with a Polytron (Brinkman) at setting 6 for 30 seconds. The membranes were washed by centrifugation for 20 minutes at 30,000 × g, followed by resuspension to twice the original volume. The homogenate was incubated at 25° for 1 hour, followed by centrifugation as above.

The resulting homogenate was then assayed for protein content according to the method described by Itzhaki et al., "A Micro-Biuret Method for Estimating Proteins," *Anal. Biochem.*, 9, 401–410 (1964). The final pellet was resuspended to a protein concentration of 10 mg protein per mL (assuming 6% of wet weight is protein) and 4 mL aliquots were rapidly frozen in liquid $N_2$.

The binding of compounds to the rat brain opiate receptor membrane preparation containing either $\delta$ or $\mu$ opioid receptors was measured using a modification of the method of C. B. Pert et al., "Properties of Opiate-Receptor Binding in Rat Brain," *Proc. Natl. Acad. Sci.*, 70, 2243–2247 (1972).

The opiate binding assays were conducted in triplicate at 37° C. in 50 mM TrisHCl buffer at pH 7.4 in a final volume of 1 mL, using varying concentrations of the compound being evaluated. Each of three tubes contained 0.8 mL of homogenate containing approximately 1 mg/mL of protein. $^3$[H]-DAMPGO (2.0 nM) and $^3$[H]-DSLET (1.0 nM) were used to label the $\mu$ and $\delta$ opiate rat brain receptors, respectively.

The "per cent displacement" of radiolabeled ligand ($^3$[H]-DAMPGO for the $\mu$ receptors and $^3$[H]-DSLET for the $\delta$ receptors) bound to the $\mu$ or $\delta$ opioid receptors by a compound was determined at different concentrations of the compound (10 $\mu$M, 1 $\mu$M, 100 nM and/or 1 nM). Because the radiolabeled ligand and the compound compete with each other for the opiate receptor binding sites, the greater the per cent of displacement of the bound radiolabeled ligand, the better the compound is in terms of its ability to bind to the opiate receptors and, thus, the more potent the compound is. "Specific binding" of a compound of the present invention to the $\mu$ or the $\delta$ opiate rat brain receptors was defined as the difference between total binding and that in the presence of 10 $\mu$M of levorphanol.

For those compounds which bound particularly well to the opiate receptors, the mean $IC_{50}$ value (that concentration of a particular compound which is required to have 50 per cent of the bound radiolabeled ligand displaced from the opiate receptors) was calculated (nM). $IC_{50}$ values were determined from log-logit plots of concentration vs. time response curves. Comparison of $IC_{50}$ values in this assay system provides a measure of the receptor specificity of the tested compounds.

Finally, for those compounds for which a mean $IC_{50}$ value was calculated for both the $\mu$ and $\delta$ opioid receptors, the ratio of the mean $IC_{50}$ values for the $\mu$ and $\delta$ opioid receptors was determined. This ratio indicates how specific a particular compound is for the $\delta$ opioid receptors. Thus, if the ratio of the mean $IC_{50}$ values is 1.0, the compound is approximately equally specific for both the $\mu$ and the $\delta$ opioid receptors. The greater the number is above 1.0, the more specific the compound is for the $\delta$ opioid receptors. The smaller the number is below 1.0, the more specific the compound is for the $\mu$ opioid receptors.

The results obtained from this opiate binding assay are shown in Table IV below, and correspond to the compound shown and described in the particular example identified below which corresponds thereto. As Table IV shows, compounds within the invention have a good affinity for both the $\mu$ and the $\delta$ opioid receptors and, thus, would be predicted on this basis to have analgesic activity.

TABLE IV

Data Obtained from the Opiate Binding Assay

| Example Number | Mean $IC_{50}$ Value (nM) | Mean $IC_{50}$ $\mu/\delta$ Ratio |
|---|---|---|
| Example 3 ($\mu$) | 62 | 6 |
| Example 3 ($\delta$) | 10 | 6 |
| Example 4 ($\mu$) | 1000 | 10 |
| Example 4 ($\delta$) | 100 | 10 |
| Example 6 ($\mu$) | 1.3 | 0.4 |
| Example 6 ($\delta$) | 3.5 | 0.4 |
| Example 8 ($\mu$) | <10 | <0.4 |
| Example 8 ($\delta$) | 25 | <0.4 |
| Example 10 ($\mu$) | <10 | <0.43 |
| Example 10 ($\delta$) | 23.1 | <0.43 |
| Example 11 ($\mu$) | 58.6 | 1.8 |
| Example 11 ($\delta$) | 32.8 | 1.8 |
| Example 13 ($\mu$) | <10 | <1.8 |
| Example 13 ($\delta$) | 5.5 | <1.8 |
| Example 14 ($\mu$) | 26.3 | 0.4 |
| Example 14 ($\delta$) | 66.3 | 0.4 |
| Example 15 ($\mu$) | 4.5 | 0.3 |
| Example 15 ($\delta$) | 14.9 | 0.3 |
| Example 18 ($\mu$) | <10 | <1.1 |
| Example 18 ($\delta$) | 9.3 | <1.1 |

TABLE IV-continued

Data Obtained from the Opiate Binding Assay

| Example Number | Mean IC$_{50}$ Value (nM) | Mean IC$_{50}$ μ/δ Ratio |
| --- | --- | --- |
| Example 20 (μ) | <10 | <0.5 |
| Example 20 (δ) | 19.4 | <0.5 |

The foregoing examples are provided to enable one of ordinary skill in the art to practice the present invention. These examples are merely illustrative, however, and should not be read as limiting the scope of the invention as it is claimed in the appended claims.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth hereinabove may be applicable as a consequence of variations in the responsiveness of the animal being treated to induce analgesia, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed, and such expected variations or differences in the results are contemplated in accordance with the objects and practices of the present invention. It is intended therefore that the invention be limited only by the scope of the claims which follow, and that such claims be interpreted as broadly as is reasonable.

What is claimed is:

1. A method for treating pain in an animal comprising administering to said animal a therapeutically-effective amount of a compound, wherein the compound is:

N-[2-[[2S-amino-3-(4-hydroxy-2,6-dimethylphenyl)-1-oxopropyl]amino]-2-methylpropyl]2-quinolinecarboxamide, hydrochloride; or N-[2-[[2S-amino-3-(4-hydroxy-2,6-dimethylphenyl)1-oxopropyl]amino]-2-methylpropyl]-3-quinolinecarboxamide, hydrochloride.

2. A pharmaceutical composition comprising a pharmaceutically-acceptable carrier and a compound, wherein the compound is:

N-[2-[[2S-amino-3-(4-hydroxy-2,6-dimethylphenyl)-1-oxopropyl]amino]-2-methylpropyl]2-quinolinecarboxamide, hydrochloride; or N-[2-[[2S-amino-3-(4-hydroxy-2,6-dimethylphenyl)-1-oxopropyl]amino]-2-methylpropyl]-3-quinolinecarboxamide, hydrochloride.

3. A compound having the structure:

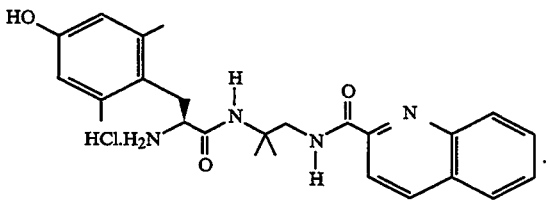

4. A compound having the structure:

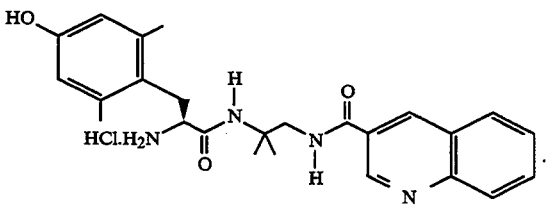

* * * * *

UNITED STATES PATENT AND TRADEMARK OFFICE
CERTIFICATE OF CORRECTION

PATENT NO. : 5,389,645          Page 1 of 2

DATED : February 14, 1995

INVENTOR(S) : Hansen, Jr., et al.

It is certified that error appears in the above-indentified patent and that said Letters Patent is hereby corrected as shown below:

Column 5, line 17, reading "chain.," should read -- chain, --.

Column 12, line 40, that part of the formula reading $$\underset{R^5 \quad R^5}{\diagup\!\!\!\diagdown} \quad \text{should read} \quad \underset{R^4 \quad R^5}{\diagup\!\!\!\diagdown}$$

Column 17, line 9, reading "abovedescribed" should read -- above-described --.

Column 28, line 2, reading "501,132):" should read -- 501.132): --.

Column 28, line 55, reading "-2=" should read -- -2- --.

Column 30, line 3, reading "153,400-408" should read -- 133, 400-408 --.

Column 34, line 5, reading "-methylpropyl]2-" should read -- -methylpropyl]-2- --.

UNITED STATES PATENT AND TRADEMARK OFFICE
CERTIFICATE OF CORRECTION

PATENT NO. : 5,389,645
DATED : February 14, 1995
INVENTOR(S) : Hansen, Jr., et al.

It is certified that error appears in the above-identified patent and that said Letters Patent is hereby corrected as shown below:

Column 34, line 7, reading "-dimethylphenyl)" should read -- -dimethylphenyl)- --.

Column 34, line 14, reading "-methylpropyl]2-" should read -- -methylpropyl]-2- --.

Signed and Sealed this

Tenth Day of October, 1995

Attest:

*Attesting Officer*

BRUCE LEHMAN

*Commissioner of Patents and Trademarks*